United States Patent [19]
Vicari et al.

[11] Patent Number: 6,037,510
[45] Date of Patent: Mar. 14, 2000

[54] CATALYTIC GAS-PHASE HYDROGENATION OF OLEFINS

[75] Inventors: Maximilian Vicari, Limburgerhof; Marc Walter, Frankenthal; Stephan Dilling, Weinheim, all of Germany

[73] Assignee: BASF Aktiengesellschaft, Ludwigshafen, Germany

[21] Appl. No.: 09/076,195

[22] Filed: May 12, 1998

[30] Foreign Application Priority Data

May 12, 1997 [DE] Germany .................. 197 19 833

[51] Int. Cl.⁷ ..................................... C07C 5/02
[52] U.S. Cl. .................. 585/263; 585/259; 585/277
[58] Field of Search .................. 585/250, 263, 585/277, 259

[56] References Cited

U.S. PATENT DOCUMENTS

| | | | |
|---|---|---|---|
| 3,775,291 | 11/1973 | Sze .................................... | 208/15 |
| 4,107,225 | 8/1978 | Debande et al. .................... | 260/683 |
| 4,124,650 | 11/1978 | Olavesen et al. .................... | 260/676 |
| 4,203,828 | 5/1980 | Bodnick et al. .................... | 208/213 |
| 4,347,392 | 8/1982 | Cosyns et al. .................... | 585/259 |
| 4,831,200 | 5/1989 | Debras et al. .................... | 585/259 |
| 5,817,901 | 10/1998 | Trambouze et al. .................... | 585/259 |

FOREIGN PATENT DOCUMENTS

| | | |
|---|---|---|
| 880595 | 4/1980 | Belgium . |
| 2707851 | 9/1977 | Germany . |
| 3010720 | 9/1981 | Germany . |
| 2072217 | 9/1981 | United Kingdom . |
| 86/05801 | 10/1986 | WIPO . |
| 97/29841 | 8/1997 | WIPO . |

OTHER PUBLICATIONS

Allinger et al., *Org. Chemie*, p. 481, 1980.

*Primary Examiner*—Bekir L. Yildirim
*Attorney, Agent, or Firm*—Keil & Weinkauf

[57] ABSTRACT

The gas-phase hydrogenation of a feed containing at least 50% by weight of at least one $C_6$–$C_{20}$-olefin with a gas containing at least hydrogen over a catalyst is carried out by a process in which the feed is introduced as a liquid into the gas.

19 Claims, No Drawings

CATALYTIC GAS-PHASE HYDROGENATION OF OLEFINS

The invention relates to a process for the gas-phase hydrogenation of olefins, the olefins not being vaporized beforehand in an evaporator.

In the oligomerization of light olefins, for example ethylene, propylene and butylene, $C_6$–$C_{20}$-olefins are obtained. These olefins are present mainly in crack gases, as formed, for example, in FCC or SC plants, or are produced by dehydrogenating the corresponding paraffins. The oligomerization of these light olefins can be carried out in the presence of a homogeneous or a heterogeneous catalyst. The resulting $C_6$–$C_{20}$-olefins can be further processed to give fuels. Isooctane is particularly suitable as a gasoline fuel component since this compound is distinguished by a high RON and high MON.

N. L. Allinger et al., Organische Chemie, page 481 et seq., de Gruyter, 1980, discloses the hydrogenation of double bonds at low pressures (from 1 to 4 bar) and at moderate temperatures (<100° C.) over noble metals of subgroup VIII of the Periodic Table (platinum, palladium and also rhodium). This prior art also describes the hydrogenation of double bonds using nickel catalysts.

In gas-phase hydrogenation processes under mild conditions, it has been necessary to date to convey the olefin-containing feed to an evaporator prior to feeding into the gas of the reaction system, in particular in the reactor, by bringing the feed from the liquid to the gaseous phase for the gas-phase hydrogenation. In general, said evaporators are heated zones which are preferably arranged upstream of the reactor and through which the hydrogenation gas flows. This preliminary vaporization entails expensive apparatus and high energy consumption and is accordingly in particular an economic disadvantage.

Belgian Patent 880,595 discloses a process for the preparation of paraffinic solvents by gas-phase hydrogenation of oligomers, in which process, however, the gas-phase hydrogenation is not carried out with the novel form of feed.

It is an object of the present invention to provide a process for the gas-phase hydrogenation of olefin-containing feeds, in which the reaction conditions, in particular temperature, pressure, hydrocarbon load, the ratio of gas to feed and the reaction procedure, in particular the method of feeding, are chosen so that the gas-phase hydrogenation can be carried out with high yields without preliminary vaporization of the feed.

We have found that this object is achieved, surprisingly, by a process for the gas-phase hydrogenation of a feed containing at least 50% by weight of at least one $C_6$–$C_{20}$-olefin by means of a gas containing at least hydrogen over a catalyst, wherein the feed is introduced as a liquid into the gas.

The abovementioned novel process for the gas-phase hydrogenation is preferably carried out over a catalyst containing at least one element of subgroup VIII of the Periodic Table in a reaction system, the gas being circulated with at least one parameter, preferably two parameters, particularly preferably all parameters, such as a molar gas/feed ratio of from 5 to 200, in a gas temperature range of from 50 to 300° C., a gas pressure range of from 1 to 20 bar, a catalyst space velocity of from 0.25 to 3 kg per l of catalyst per h.

I. Olefin Feed

According to the invention, the feed contains any $C_6$–$C_{20}$-olefins known to a person skilled in the art. The above definition of olefins includes olefins having one or more double bonds and branched, straight-chain and cyclic olefins. The feed used according to the invention contains at least 50, preferably at least 75, particularly preferably at least 90, % by weight of the abovementioned olefins or of the olefins stated below.

A feed preferred according to the invention contains in general $C_6$–$C_{20}$-olefins, preferably $C_6$–$C_{16}$-olefins, especially $C_6$–$C_{13}$-olefins, particularly preferably $C_7$–$C_8$-olefins or $C_{11}$–$C_{13}$-olefins having from 1 to 3, preferably 1 or 2, double bonds, particularly preferably one double bond, and mixtures thereof.

A further feed preferred according to the invention preferably contains branched $C_6$–$C_{20}$-olefins, preferably $C_6$–$C_{16}$-olefins, especially $C_6$–$C_{13}$-olefins, particularly preferably $C_7$- or $C_8$- or $C_{11}$- to $C_{13}$-olefins having 3, preferably 2, double bonds, particularly preferably one double bond.

Another feed preferred according to the invention contains from 60 to 80% by weight, based on the total feed, of a branched $C_6$–$C_{20}$-α-olefin, preferably $C_6$–$C_{16}$-α-olefin, especially $C_6$–$C_{13}$-α-olefin, particularly preferably $C_7$–$C_9$-α-olefin having from 1 to 3, preferably 1 or 2, double bonds, particularly preferably one double bond.

Furthermore, a novel preferred feed contains from 40 to 20% by weight, based on the total feed, of a branched $C_6$–$C_{20}$-β-olefin, preferably $C_6$–$C_{16}$-β-olefin, especially $C_6$–$C_{13}$-β-olefin, particularly preferably $C_7$–$C_9$-β-olefin having from 1 to 3, preferably 1 or 2, double bonds, particularly preferably one double bond.

A feed particularly preferred according to the invention contains both the branched α-olefin and the branched β-olefin of the two sections above.

According to the invention, a feed furthermore preferably contains from 60 to 80% by weight, based on the total feed, of a $C_8$-α-olefin having one double bond, it being particularly preferable if the abovementioned olefin is branched. Also preferred according to the invention is a feed which contains from 40 to 20% by weight, based on the total feed, of a $C_8$-β-olefin having one double bond, it being particularly preferable if this β-olefin is branched. A feed preferred over and above these two novel feeds contains both the abovementioned $C_8$-α-olefin and the abovementioned $C_8$-β-olefin, each having one double bond, particularly preferably in the two last-mentioned % by weight ranges, based in each case on the total feed.

Another feed preferred according to the invention contains from 60 to 80, preferably from 65 to 75, % by weight, based on the total feed, of a $C_8$-α-olefin having a $C_5$ main chain and one double bond, particularly preferably 2,4,4-trimethyl-1-pentene. A feed also preferred according to the invention contains from 40 to 20, preferably from 35 to 25, % by weight, based on the total feed, of a $C_8$-β-olefin having a $C_5$ main chain and one double bond, particularly preferably 2,4,4-trimethyl-2-pentene. A feed preferred to these novel feeds stated in this section is one which contains both the $C_8$-α-olefin having a $C_5$ main chain and one double bond and the $C_8$-β-olefin having a $C_5$ main chain and one double bond, particularly preferably 2,4,4-trimethyl-1-pentene and 2,4,4-trimethyl-2-pentene, in the % by weight ranges stated at the beginning of this section.

A further novel feed contains at least 90% of a $C_8$- or $C_{12}$-olefin cut.

Other preferred feeds are those which correspond to the $C_6$–$C_{20}$-olefin fractions, preferably $C_6$–$C_{16}$-olefin fractions, as obtained as main products or byproducts in the oligomerization of light olefins, for example ethylene, propylene and butylene. $C_6$–$C_{20}$-Olefin fractions are particularly preferred, especially $C_6$–$C_{16}$-olefin fractions, as obtained as main products or byproducts in the large-scale industrial oligomerization of light olefins, for example ethylene, propylene and butylene, in particular in the large-scale industrial processes such as the Polygas processes of UOP Inc., the Octol process of Hüls AG and the Dimersol processes of IFP.

II. Gas

Preferably exclusively hydrogen as well as hydrogen mixed with inert gases are suitable as gas for the novel process for the gas-phase hydrogenation of olefins. Inert gases preferred according to the invention are $CH_4$, nitrogen and noble gases, preferably nitrogen and argon, particularly preferably nitrogen, and moreover preferably $CH_4$ or mixtures thereof. For the novel hydrogenation process, the gas must contain at least a stoichiometric amount of hydrogen required for the number of double bonds according to the degree of hydrogenation. Where all double bonds of a feed are to be hydrogenated, it is accordingly necessary for at least the stoichiometric amount of hydrogen corresponding to the number of double bonds in this feed to be present in the gas. The hydrogen/inert gas ratios preferred according to the invention in the gas are shown in Table 1, the stated percentages by weight being based on the total gas.

TABLE 1

| Gas | % by weight | Preferred % by weight | Particularly preferred % by weight |
|---|---|---|---|
| $H_2$ gas | 50 to <100 | 80 to <100 | 90 to <100 |
| Inert gas | >0 to 50 | >0 to 20 | >0 to 10 |

III. Catalyst

The catalysts familiar to a person skilled in the art and containing at least one element of subgroup VIII are suitable for the novel process for the gas-phase hydrogenation of olefins. In the novel process for the gas-phase hydrogenation, the preferably heterogeneous catalysts may be used in the form of both supported and preferably unsupported catalysts.

According to the invention, it is preferable if, in addition to at least one element of subgroup VIII, at least one element selected from the group consisting of the elements of main groups III and IV and of subgroup IV are also present in the catalyst. It is also preferable if, in addition to at least one element of subgroup VIII, one element each of main groups III and IV and of subgroup IV are present in the catalyst. Catalysts particularly preferably used in the novel process are shown in Table 2 below, the stated percentages by weight being based on the total catalyst.

TABLE 2

| Elements, preferably the oxides thereof | Preferred [% by weight]* | Particularly preferred [% by weight]* |
|---|---|---|
| Subgroup VIII, preferably nickel | 55 to 100 | 60 to 97 |
| Main group IV, preferably silicon | 0 to 25 | 1 to 20 |
| Main group III, preferably aluminum | 0 to 10 | 1 to 10 |
| Subgroup IV, preferably zirconium | 0 to 10 | 1 to 10 |

*Based on nickel oxide, silicon oxide, aluminum oxide, zirconium oxide

Catalysts particularly preferred according to the invention contain from 65 to 80% by weight, calculated as nickel oxide, of nickel, from 10 to 25% by weight, calculated as silicon dioxide, of silicon, from 2 to 10% by weight, calculated as zirconium oxide, of zirconium and from 0 to 10% by weight, calculated as aluminum oxide, of aluminum, preferably with the proviso that the sum of the contents of silicon dioxide and aluminum oxide is at least 15% by weight, based on the total mass of the catalyst, preferably obtainable by adding an acidic, aqueous solution of nickel salts, zirconium salts and, if required, aluminum salts to a basic, aqueous solution with suspension of silicon compounds and, if required, aluminum compounds, the pH of the mixture thus obtained preferably being reduced to at least 8.5 and then being brought to 7–8 by adding further basic solution. The solid thus precipitated can then be isolated, dried, molded to give the desired catalyst shape and then calcined.

IV. Gas/Feed Ratio

In the novel process for the gas-phase hydrogenation of olefins, the molar gas/feed ratio must preferably be adjusted so that the feed can be introduced, into the gas, as a liquid, preferably at a temperature which is below its boiling point at the pressure prevailing in the gas circulation of the reactor system, and is present in gaseous form in the gas of the gas circulation. It is accordingly preferable to ensure that the partial pressure of the feed in the gas is in a range in which the gas can absorb the feed in gaseous form without preliminary vaporization being necessary, and gas and feed preferably form a homogeneous phase in the gas circulation. Where the gas of the novel process also contains inert gas in addition to hydrogen, it is preferable if the amount of inert gas contained in the gas is also taken into account for establishing the molar gas/feed ratio. Furthermore, depending on the completeness of the hydrogenation, it must be ensured that the amount of hydrogen supplied is at least sufficient to enable the desired number of double bonds to be hydrogenated. The molar gas/feed ratio may be stated both as a molar hydrogen/double bond ratio and—as usual in industry—as the ratio of gas volume in cubic meters at atmospheric pressure per kg of feed.

Preferably, the molar gas/feed ratio is from 30 to 150, preferably from 40 to 130, particularly preferably from 50 to 100, more preferably from 60 to 90.

Preferably, the molar gas/feed ratio as a molar hydrogen/double bond ratio is generally from 5 to 200, particularly when the gas contains at least 90% by weight of hydrogen gas. In a preferred embodiment of the novel process, the molar hydrogen/double bond ratio is from 30 to 100, preferably from 40 to 130, particularly preferably from 50 to 100, more preferably from 60 to 90.

In the case of a feed which contains at least 90% by weight of a $C_8$-olefin, it is furthermore particularly preferred according to the invention to use a ratio of gas volume to feed weight of from 1 to 30, preferably from 5 to 25, particularly preferably from 10 to 20, $m^3$ (S.T.P.)/kg, preferably with a hydrogen content of at least 90% by weight in the gas. Where the feed contains at least 90% of a $C_{12}$-olefin, it is particularly preferred according to the invention to establish a ratio of gas volume to feed weight of from 1 to 30, preferably from 2 to 20, particularly preferably from 5 to 15, $m^3$ (S.T.P.)/kg in the novel process, preferably with a hydrogen content of at least 90% by weight in the gas.

V. Temperature

In the novel process for the catalytic hydrogenation of olefins, the temperature established usually depends on the catalyst used and on the feed employed. Here, it is preferable to regulate the temperature in the range in which the catalyst is active. Within this temperature range in turn, the temperatures in the lower part of this range are preferred, especially since the total reaction system experiences lower thermal loads at low temperature and the formation of byproducts formed at high temperatures is suppressed. Thus, the novel process for the gas-phase hydrogenation and the introduction of the feed into the gas are carried out at a gas temperature of from 60 to 200° C., preferably from 70 to 130° C., particularly preferably from 70 to 90° C. or from 110 to 130° C.

VI. Pressure

The novel process for the gas-phase hydrogenation of olefins is preferably carried out at very low pressures so that those parts of the reaction system, referred to below as the hydrogenation plant, which are exposed to the pressure do not suffer any high material stress and accordingly the hydrogenation plant can be produced from less pressure-stable elements, leading in the end to lower costs for plant construction and plant operation. On the other hand, depending on the catalyst type, it is often necessary to carry out the hydrogenation at slightly superatmospheric pressures. The novel process of the gas-phase hydrogenation is therefore preferably carried out at a gas pressure of from 2 to 20, preferably from 2.5 to 15, particularly preferably from 3 to 10, more preferably from 4 to 7, bar.

VII. Catalyst Space Velocity

The catalyst space velocity in the novel process of the gas-phase hydrogenation of olefins is dependent in each case on the catalyst used. It is however preferable if it is from 0.3 to 2.5, preferably from 0.5 to 2, particularly preferably from 0.6 to 1.4, kg per l of catalyst per h.

VIII. Gas Circulation

In the novel process for gas-phase hydrogenation of olefins, the gas described above is preferably circulated. This means in particular that, after it has left the reactor, the gas is freed from the reaction products of the hydrogenation reaction, the hydrogen consumed by the hydrogenation reaction is replaced and the gas is then recycled to the hydrogenation reaction.

IX. Feed

In the novel process for the gas-phase hydrogenation of olefins, the feed can be introduced in any section of the gas circulation. However, it is preferable according to the invention if the feed is introduced in the section which begins after the separation of the hydrogenation zone and ends with the reactor. It is particularly preferred according to the invention if the feed is introduced into the reactor and particularly preferably into the upper region of the reactor.

In the novel hydrogenation process, the feed is preferably introduced into the gas circulation at a feed temperature which is below its boiling point at the pressure prevailing in the gas circulation, the feed preferably being essentially gaseous after introduction into the gas circulation. The feed is preferably introduced at a pressure higher than that prevailing in the gas circulation and/or reactor during the hydrogenation. The feed is preferably effected at from 1.01 to 10, particularly preferably from 1.5 to 5, times the pressure of the gas circulation and/or of the reactor during the hydrogenation.

It is furthermore preferred according to the invention if the feed is effected by spraying in by means of a nozzle. By using a nozzle, it is possible to introduce the feed in the form of very small, finely divided liquid particles into the gas of the gas circulation so that it is no longer necessary to vaporize the feed in an evaporation zone before introduction into the gas circulation. The liquid particles produced by the nozzle during introduction of the feed into the gas circulation preferably have an average particle size which makes it possible for the feed to be essentially gaseous after introduction into the gas circulation. In this context, an average particle size of from 1 to 100, preferably from 1.1 to 50, particularly preferably from 1.2 to 20, $\mu$m is advantageous.

According to the present invention the term "without preliminary vaporisation" means that the hydrocarbon feed and/or the hydrocarbon mixture feed is liquid during being fed in the hydrogenation device, but is in an gaseous state in the above-defined gas.

X. Hydrogenation Plant

A preferred embodiment of a reaction system for carrying out the novel gas-phase hydrogenation process consists essentially of a gas circulation (1), in which the gas is conveyed in a gas flow direction and which, in the gas flow direction, comprises a reactor (2), preferably an adiabatic reactor, a heat exchanger (3), a separator (4), a fresh gas supply (5), a circulation gas compressor (6), a feed metering unit, consisting of a feed reservoir (7) and a metering pump (8), and a heat exchanger (9). The separator (4) is followed by a further separator (10) for separating gas or hydrogen (11) from the resulting hydrogenation product (12). After the separator (4), the byproducts (13) formed in the reaction are removed from the gas circulation (1). The individual assemblies of the plant described above are formed from components and materials which are known to the plant constructor and are suitable for withstanding the reaction conditions and in particular the temperatures and pressures of the novel process in a suitable manner.

The two non-limiting Examples which follow illustrate the invention.

EXAMPLES

The two Examples were carried out using the reaction parameters stated in Tables 3, 3b, 3c and 3d for Example 1 and 4a, 4b and 4c for Example 2, the reaction being carried out in an experimental reactor present in a gas circulation. The experimental reactor consisted of a steel tube having a cross-section of 30 cm and a length of 1 m. Furthermore, it was heated by means of an electrical heating apparatus. In both cases, the catalyst used was a precipitated nickel catalyst in the form of 1.5 mm extrudates, is composed of 75% by weight of Ni, 15% by weight of Si, 5% by weight of Al and 5% by weight of Zr, based in each case on the oxides.

Example 1

TABLE 3a

| Starting materials | |
|---|---|
| Composition | % by weight |
| Olefins | |
| 2,4,4-Trimethyl-1-pentene | 69.3 |
| 2,4,4-Trimethyl-2-pentene | 19.3 |
| Other $C_8$-olefins | 2.0 |
| $C_{12}$-Olefins | 7.6 |
| $C_{16}$-Olefins | 1.0 |
| Other compounds | |
| $C_4$-Hydrocarbons | 0.6 |
| MTBE | 0.2 |

TABLE 3b

| Properties of the starting materials | |
|---|---|
| Bromine number (g/100 g) | 134.7 |
| Density (15° C.) | 0.7241 |
| Refractive index | 1.4130 |

TABLE 3c

| Reaction conditions | |
|---|---|
| Pressure (bar) | 5 |
| Inlet temperature (° C.) | 90 |
| Hydrocarbon loading (kg per l of catalyst per h) | 1 |
| Hydrogen/hydrocarbon ratio (m³ (S.T.P.)/kg) | 16 |

TABLE 3c-continued

Reaction conditions

| Catalyst | Precipitated nickel catalyst according to EP 672 452 |
|---|---|
| Δ T in the reactor (° C.) | 43 |

TABLE 3d

Product properties

| Bromine number (mg/100 g) | 0 |
|---|---|
| Density (15° C.) | 0.7036 |
| Refractive index (20° C.) | 1.3961 |

Example 2

TABLE 4a

Properties of the starting materials

Starting material: $C_{12}$-olefin cut having a purity of 99% by weight

| Bromine number (g/100 g) | 94.9 |
|---|---|
| Density (15° C.) | 0.7733 |
| Refractive index (20° C.) | 1.4376 |

TABLE 4b

Reaction conditions

| Pressure (bar) | 5 |
|---|---|
| Inlet temperature (° C.) | 120 |
| Hydrocarbon loading (kg per 1 of catalyst per h) | 1 |
| Hydrogen/hydrocarbon ratio (m³ (S.T.P.)/kg) | 9.5 |
| Catalyst | Precipitated nickel catalyst according to EP 672 452 |
| Δ T in the reactor (° C.) | 28 |

TABLE 4c

Product properties

| Bromine number (mg/100 g) | 0 |
|---|---|
| Density (15° C.) | 0.7616 |
| Refractive index (20° C.) | 1.4252 |

The two Examples show that, with the use of the novel process for the gas-phase hydrogenation of olefins, complete olefin degradation, ie. quantitative conversion of the olefin used, takes place under mild reaction conditions.

We claim:

1. A process for the gas-phase hydrogenation of a feed containing at least 50% by weight of at least one $C_6$–$C_{20}$-olefin by means of a gas containing at least hydrogen over a catalyst, wherein the feed is introduced as a liquid into the gas.

2. A process as claimed in claim 1, wherein the gas-phase hydrogenation is carried out over a catalyst containing at least one element of subgroup VIII in a reaction system, the gas being circulated with at least one of the parameters a molar gas/feed ratio of from 5 to 200, a gas temperature range of from 50 to 300° C., a gas pressure range of from 1 to 20 bar, a catalyst space velocity of from 0.25 to 3 kg per 1 of catalyst per h.

3. A process as claimed in claim 1, wherein the feed contains at least 90% by weight of a $C_8$- or $C_{12}$-olefin.

4. A process as claimed in claim 1, wherein the gas contains hydrogen from 50 to <100 wt.-% and an inert gas from <0 to 50 wt.-%, based on the total gas.

5. A process as claimed in claim 4, wherein the inert gas used is argon, nitrogen, $CH_4$ or a mixture thereof.

6. A process as claimed in claim 1, wherein the catalyst used is one which contains at least one element each of main groups III and IV and at least one element of subgroup IV in addition to at least one element of subgroup VIII.

7. A process as claimed in claim 6, wherein the catalyst used contains at least the elements Ni, Si, Al and Zr.

8. A process as claimed in claim 1, wherein the gas-phase hydrogenation and the introduction of the feed into the gas are carried out at a molar gas/feed ratio of from 30 to 150.

9. A process as claimed in claim 1, wherein the gas-phase hydrogenation and the introduction of the feed into the gas are carried out at a gas temperature of from 60 to 150° C.

10. A process as claimed in claim 1, wherein the gas-phase hydrogenation is carried out at from 2 to 20 bar.

11. A process for the gas-phase hydrogenation of a feed containing at least 50% by weight of at least one $C_6$–$C_{20}$-olefin by means of a gas containing at least hydrogen over a catalyst, wherein the feed is introduced as a liquid into the gas, and wherein the gas-phase hydrogenation is carried out over a catalyst containing at least one element of subgroup VIII in a reaction system, the gas being circulated with at least one of the parameters a molar gas/feed ratio of from 5 to 200, a gas temperature range of from 50 to 300° C., a gas pressure range of from 1 to 20 bar, a catalyst space velocity of from 0.25 to 3 kg per 1 of catalyst per h.

12. A process as claimed in claim 11, wherein the feed contains at least 90% by weight of a $C_8$- or $C_{12}$-olefin.

13. A process as claimed in claim 11, wherein the gas contains hydrogen from 50 to <100 wt.-% and an inert gas from <0 to 50 wt.-%, based on the total gas.

14. A process as claimed in claim 11, wherein the catalyst used is one which contains at least one element each of main groups III and IV and at least one element of subgroup IV in addition to at least one element of subgroup VIII.

15. A process as claimed in claim 11, wherein the gas-phase hydrogenation and the introduction of the feed into the gas are carried out at a molar gas/feed ratio of from 30 to 150.

16. A process as claimed in claim 11, wherein the gas-phase hydrogenation and the introduction of the feed into the gas are carried out at a gas temperature of from 60 to 150° C.

17. A process as claimed in claim 11, wherein the gas-phase hydrogenation is carried out at from 2 to 20, preferably from bar.

18. A process as claimed in claim 11, wherein the gas-phase hydrogenation is carried out at a catalyst space velocity of from 0.2 to 2.5 kg per 1 of catalyst per h. and a feed temperature which is below its boiling point at the pressure prevailing in the gas.

19. A process as claimed in claim 11, wherein the feed is introduced into a reactor.

* * * * *

UNITED STATES PATENT AND TRADEMARK OFFICE
CERTIFICATE OF CORRECTION

PATENT NO. : 6,037,510
DATED : March 14, 2000
INVENTOR(S) : VICARI et al

It is certified that error appears in the above-identified patent and that said Letters Patent is hereby corrected as shown below:

Column 8, claim 17, lines 55 and 56, delete "preferably from"

Signed and Sealed this

Sixth Day of February, 2001

Attest:

Q. TODD DICKINSON

Attesting Officer
Director of Patents and Trademarks